US012589199B2

(12) United States Patent
Munsinger et al.

(10) Patent No.: US 12,589,199 B2
(45) Date of Patent: Mar. 31, 2026

(54) APPARATUS FOR INCREASED DYE FLOW

(71) Applicant: BOSTON SCIENTIFIC SCIMED, INC., Maple Grove, MN (US)

(72) Inventors: Joel R. Munsinger, Blaine, MN (US); Derek C. Sutermeister, Ham Lake, MN (US); Mark Steven Smith, Coon Rapids, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1190 days.

(21) Appl. No.: 14/980,437

(22) Filed: Dec. 28, 2015

(65) Prior Publication Data

US 2016/0175516 A1     Jun. 23, 2016

(51) Int. Cl.
A61M 5/00        (2006.01)
A61B 18/00        (2006.01)
A61B 18/14        (2006.01)

(52) U.S. Cl.
CPC ......... *A61M 5/007* (2013.01); *A61B 18/1492* (2013.01); *A61B 2018/00214* (2013.01); *A61B 2018/00404* (2013.01); *A61B 2018/00434* (2013.01); *A61B 2018/00505* (2013.01); *A61B 2018/00791* (2013.01); *A61B 2218/002* (2013.01); *A61M 2210/1078* (2013.01)

(58) Field of Classification Search
None
See application file for complete search history.

(56) References Cited

U.S. PATENT DOCUMENTS

| 5,370,617 A | * | 12/1994 | Sahota | A61M 25/104 604/102.02 |
| 7,766,961 B2 | | 8/2010 | Patel et al. | |
| 2004/0122462 A1 | * | 6/2004 | Bakos | A61M 16/0429 606/191 |
| 2004/0158270 A1 | * | 8/2004 | Wyzgala | A61B 17/320758 606/170 |
| 2004/0249342 A1 | * | 12/2004 | Khosravi | A61M 25/10182 604/96.01 |
| 2005/0288632 A1 | * | 12/2005 | Willard | A61M 25/10 604/103.01 |
| 2008/0208310 A1 | * | 8/2008 | McDermott | A61F 2/01 623/1.11 |
| 2010/0069820 A1 | * | 3/2010 | Zotz | A61F 2/064 604/8 |
| 2010/0331817 A1 | * | 12/2010 | Schaeffer | A61M 25/1011 604/509 |
| 2011/0160662 A1 | * | 6/2011 | Stout | A61M 25/0097 604/122 |
| 2011/0208129 A1 | * | 8/2011 | Bonnette | A61M 39/0613 604/247 |
| 2013/0165926 A1 | | 6/2013 | Mathur et al. | |

(Continued)

*Primary Examiner* — Christopher Koharski
*Assistant Examiner* — Farouk A Bruce
(74) *Attorney, Agent, or Firm* — Seager, Tufte & Wickhem, LLP

(57)        ABSTRACT

Elongate tubular medical devices having increased fluid flow are disclosed. The elongate devices may have a parking space within a lumen for withdrawing a treatment device from the body while retaining the treatment device within the elongate device. The parking space may provide for a fluid flow through the elongate device that approximates a fluid flow through the elongate device in the absence of the treatment device.

15 Claims, 16 Drawing Sheets

(56)         References Cited

U.S. PATENT DOCUMENTS

2014/0081134 A1*   3/2014   Fortson ............... A61M 25/003
                                                          600/435
2014/0107639 A1     4/2014   Zhang et al.
2015/0173782 A1*   6/2015   Garrison ................ A61B 17/22
                                                          606/127
2015/0297290 A1*   10/2015   Beeckler ........... A61B 18/1477
                                                          606/34

* cited by examiner

APPARATUS FOR INCREASED DYE FLOW

CROSS-REFERENCE TO RELATED APPLICATIONS

This Application claims the benefit U.S. Provisional Application No. 62/095,643, filed Dec. 22, 2014 and entitled "Apparatus for Increased Dye Flow", which is hereby incorporated by reference in its entirety.

TECHNICAL FIELD

The invention relates generally to medical devices and more specifically to medical devices configured for increased fluid flow around a treatment device within the catheter.

BACKGROUND

A wide variety of intracorporeal medical devices have been developed for medical use, for example, intravascular use. Some of these devices include guidewires, catheters, guide catheters, guide sheaths and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

The disclosure is directed to several alternative designs, materials, and methods of using medical device structures and assemblies.

In a first example, a catheter having increased fluid flow around a treatment device within the catheter comprises an elongate member having a distal region configured to be disposed within a patient's body and a proximal region configured to be disposed outside a patient's body, the elongate member having a lumen extending therethrough, wherein fluid injected through the lumen in the distal region has a first flow rate in the absence of a treatment device that is insertable through the elongate member during a treatment procedure, wherein the lumen in the proximal region defines a parking space configured to contain the treatment device within the lumen but external to the patient's body, the parking space having a diameter and a length such that when the treatment device is in the parking space, fluid injected through the lumen proximal of the parking space flows around the treatment device and achieves a second flow rate in the distal region that is substantially the same as the first flow rate, and a port in fluid communication with the lumen.

Alternatively or additionally, the proximal region has a length of about 10 cm to about 15 cm and the distal region has a length of about 40 cm to about 50 cm.

Alternatively or additionally, the elongate member is devoid of other lumens.

Alternatively or additionally, the elongate member has a first outer diameter in the distal region and a second outer diameter in the proximal region, wherein the second outer diameter is larger than the first outer diameter.

Alternatively or additionally, the port is positioned distal of the parking space.

Alternatively or additionally, the elongate member includes a transition region between the proximal region and the distal region, wherein the lumen has a first diameter in the distal region and a second diameter in the proximal region, wherein the second diameter is larger than the first diameter, wherein the diameter of the lumen in the transition region increases between the first and second diameters.

Alternatively or additionally, the elongate member has an outer layer, and inner layer, and an intermediate layer, wherein the outer and inner layers extend along the distal region, the transition region, and the proximal region, and the intermediate layer extends from the transition region through the distal region, wherein the intermediate layer provides a change in lumen diameter from the first diameter to the second diameter.

Alternatively or additionally, the catheter further comprises one or more side fluid path in the proximal region, the one or more side fluid path extending adjacent to the lumen and joining a first location of the lumen to a second location of the lumen, wherein the first location is distal of the parking space and the second location is proximal of the parking space, wherein the port is disposed near a proximal end of the proximal region.

Alternatively or additionally, a catheter having increased fluid flow around a treatment device within the catheter, comprises a elongate member having a distal region configured to be disposed within a patient's body and a proximal region configured to be disposed outside a patient's body, and a lumen extending therebetween, one or more side fluid path in the proximal region, the one or more side fluid path extending adjacent to the lumen and joining a first location of the lumen to a second location of the lumen, wherein the first and second locations are spaced apart axially along the lumen, and a port in fluid communication with the lumen, the port disposed near a proximal end of the proximal region.

Alternatively or additionally, the first location is proximal of the second location and the first location is spaced about 5 cm to about 10 cm from a proximal end of the elongate member.

Alternatively or additionally, the one or more side fluid path includes first and second side fluid paths, wherein a combined cross-sectional area of the first and second side fluid paths is equal to or greater than a cross-sectional area of the lumen in the distal region.

Alternatively or additionally, at least a portion of the proximal region of the elongate member and the one or more side fluid path are disposed within an accessory device connectable with a proximal end of the elongate member, the accessory device having an accessory lumen connectable to the lumen in the elongate member, wherein the one or more side fluid path extends adjacent to the accessory lumen, the one or more side fluid path joining a first location of the accessory lumen to a second location of the accessory lumen, wherein the first and second locations are spaced apart axially along the accessory device.

Alternatively or additionally, the first and second locations are spaced apart about 4 cm to about 6 cm.

Alternatively or additionally, the first location is proximal of the second location and the first location is spaced about 1 cm to about 2 cm from a proximal end of the accessory device.

Alternatively or additionally, a catheter having increased fluid flow around a treatment device within the catheter comprises an elongate member having a distal region configured to be disposed within a patient's body and a proximal region configured to be disposed outside a patient's body, the elongate member having a lumen extending therethrough, wherein the lumen has a first diameter in the distal region and a second diameter in the proximal region, wherein the second diameter is larger than the first diameter, wherein the elongate member has a constant outer diameter along its length, wherein fluid injected through the lumen in the distal region has a first flow rate in the absence of a treatment device that is insertable through the elongate member during a treatment procedure, wherein the lumen in the proximal region defines a parking space configured to contain the treatment device within the lumen but external to the patient's body, the parking space having a diameter and a length such that when the treatment device is in the parking space, fluid injected through the lumen proximal of the parking space flows around the treatment device and achieves a second flow rate in the distal region that is substantially the same as the first flow rate, and a port in fluid communication with the lumen.

Alternatively or additionally, a catheter having increased fluid flow around a treatment device within the catheter comprises an elongate member having a distal region configured to be disposed within a patient's body and a proximal region configured to be disposed outside a patient's body, the elongate member having a lumen extending therethrough, wherein fluid injected through the lumen in the distal region has a first flow rate in the absence of a treatment device that is insertable through the elongate member during a treatment procedure, wherein the lumen in the proximal region defines a parking space configured to contain the treatment device within the lumen but external to the patient's body, the parking space having a diameter and a length such that when the treatment device is in the parking space, fluid injected through the lumen proximal of the parking space flows around the treatment device and achieves a second flow rate in the distal region that is substantially the same as the first flow rate, and a port in fluid communication with the lumen.

Alternatively or additionally, the elongate member includes a transition region between the proximal region and the distal region, wherein the lumen has a first diameter in the distal region and a second diameter in the proximal region, wherein the second diameter is larger than the first diameter, wherein the diameter of the lumen in the transition region increases between the first and second diameters.

Alternatively or additionally, the elongate member has an outer layer, and inner layer, and an intermediate layer, wherein the outer and inner layers extend along the distal region, the transition region, and the proximal region, and the intermediate layer extends from the transition region through the distal region, wherein the intermediate layer provides a change in lumen diameter from the first diameter to the second diameter.

Alternatively or additionally, the port is positioned distal of the parking space.

Alternatively or additionally, the lumen has a substantially constant diameter throughout the distal and proximal regions, the catheter further comprising one or more side fluid path in the proximal region, the one or more side fluid path extending adjacent to the lumen and joining a first location of the lumen to a second location of the lumen, wherein the first location is distal of the parking space and the second location is proximal of the parking space, wherein the port is disposed near a proximal end of the proximal region.

Alternatively or additionally, the one or more side fluid path, the parking space, and the port are disposed in an accessory device configured to be coupled to a proximal end of the elongate member, the accessory device having an accessory lumen sized and shaped to match the lumen in the elongate member, wherein the one or more side fluid path is disposed adjacent to the accessory lumen.

Alternatively or additionally, the proximal region has a length of about 10 cm to about 15 cm and the distal region has a length of about 40 cm to about 50 cm.

Alternatively or additionally, the elongate member is devoid of other lumens.

Alternatively or additionally, the elongate member has a first outer diameter in the distal region and a second outer diameter in the proximal region, wherein the second outer diameter is larger than the first outer diameter.

Alternatively or additionally, a catheter having increased fluid flow around a treatment device within the catheter comprises a elongate member having a distal region configured to be disposed within a patient's body and a proximal region configured to be disposed outside a patient's body, and a lumen extending therebetween, one or more side fluid path in the proximal region, the one or more side fluid path extending adjacent to the lumen and joining a first location of the lumen to a second location of the lumen, wherein the first and second locations are spaced apart axially along the lumen, and a port in fluid communication with the lumen, the port disposed near a proximal end of the proximal region.

Alternatively or additionally, the first and second locations are spaced apart about 4 cm to about 6 cm along the lumen.

Alternatively or additionally, the first location is proximal of the second location and the first location is spaced about 5 cm to about 10 cm from a proximal end of the elongate member.

Alternatively or additionally, the one or more side fluid path includes first and second side fluid paths, wherein a combined cross-sectional area of the first and second side fluid paths is equal to or greater than a cross-sectional area of the lumen in the distal region.

Alternatively or additionally, a method of imaging a treatment site using a elongate member while a treatment device is disposed within the elongate member comprises inserting the elongate member through an incision in a patient's skin to the treatment site, wherein a distal region of the elongate member is positioned within the patient's body and a proximal region of the elongate member is positioned outside the body, inserting the treatment device through a lumen in the elongate member, wherein the treatment device includes an element that occupies a majority of a cross-sectional area of the lumen, performing a procedure at the treatment site using the treatment device, withdrawing the treatment device such that the element is disposed in a parking space defined by the lumen in the proximal region of the elongate member, outside the body, and inserting imaging fluid through the elongate member lumen while the element remains in the parking space in the proximal region of the elongate member.

Alternatively or additionally, inserting imaging fluid includes inserting imaging fluid into a side port disposed near a distal end of the proximal region of the elongate member such that the imaging fluid enters the lumen distal of the parking space.

Alternatively or additionally, the lumen in the distal region has a first diameter and the lumen in the proximal region has a second diameter, wherein the second diameter is larger than the first diameter, wherein the parking space has the second diameter, wherein withdrawing the treatment device includes withdrawing the treatment device until the element is positioned within the parking space.

Alternatively or additionally, the elongate member further comprises a transition region between the distal and proximal regions, wherein the lumen in the transition region increases from the first diameter to the second diameter, wherein inserting the elongate member includes inserting the elongate member until the distal region is within the body and the transition region and proximal region are outside the body.

Alternatively or additionally, inserting imaging fluid includes inserting imaging fluid into a port disposed adjacent a proximal end of the elongate member, wherein a proximal region of the elongate member includes a main lumen and at least one side fluid path extending adjacent to the main lumen, the at least one side fluid path joining a first location of the main lumen to a second location of the main lumen, wherein the first and second locations are spaced apart axially a distance at least as great as a length of the parking space.

Alternatively or additionally, the treatment site is a first renal artery and the treatment device is a renal nerve ablation device, the method further comprising, after the step of inserting imaging fluid, advancing the treatment device through the elongate member to a second renal artery.

Alternatively or additionally, inserting the treatment device through a lumen in the elongate member includes coupling an accessory device to a proximal end of the elongate member, the accessory device having a distal end, a proximal end, an accessory lumen extending therebetween that defines the parking space, and at least one side fluid path extending adjacent to the accessory lumen, the at least one side fluid path joining a first location of the accessory lumen distal of the parking space to a second location of the accessory lumen proximal of the parking space, wherein withdrawing the treatment device includes withdrawing the treatment device into the parking space, wherein inserting imaging fluid includes inserting imaging fluid through the proximal end of the accessory device.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

6

Figure 13:
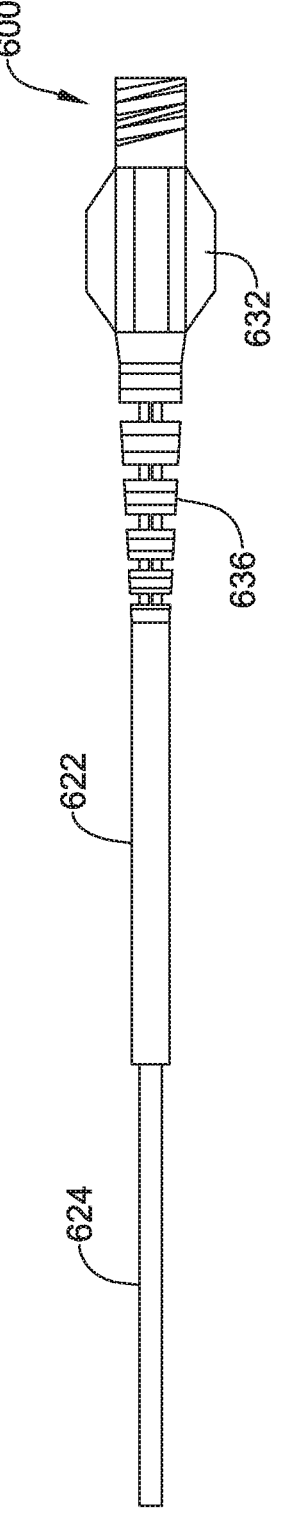

FIG. 13 is a perspective view of another example guide sheath; and

Figure 14A:
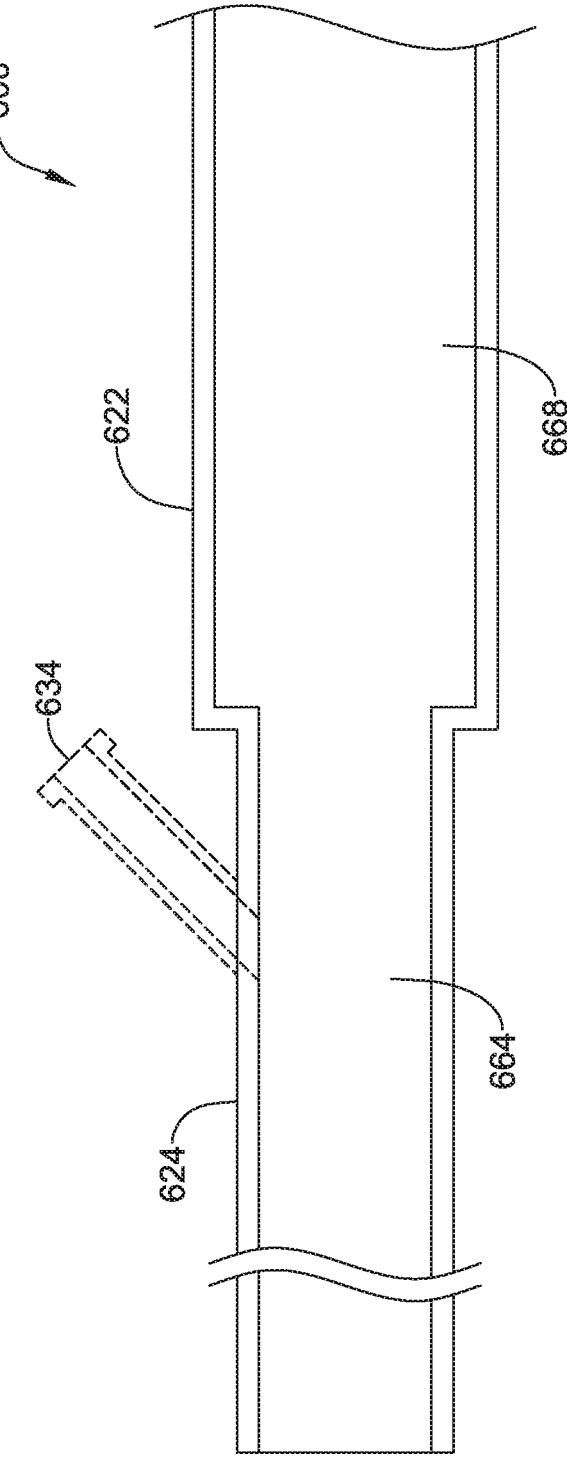
Figure 14B:
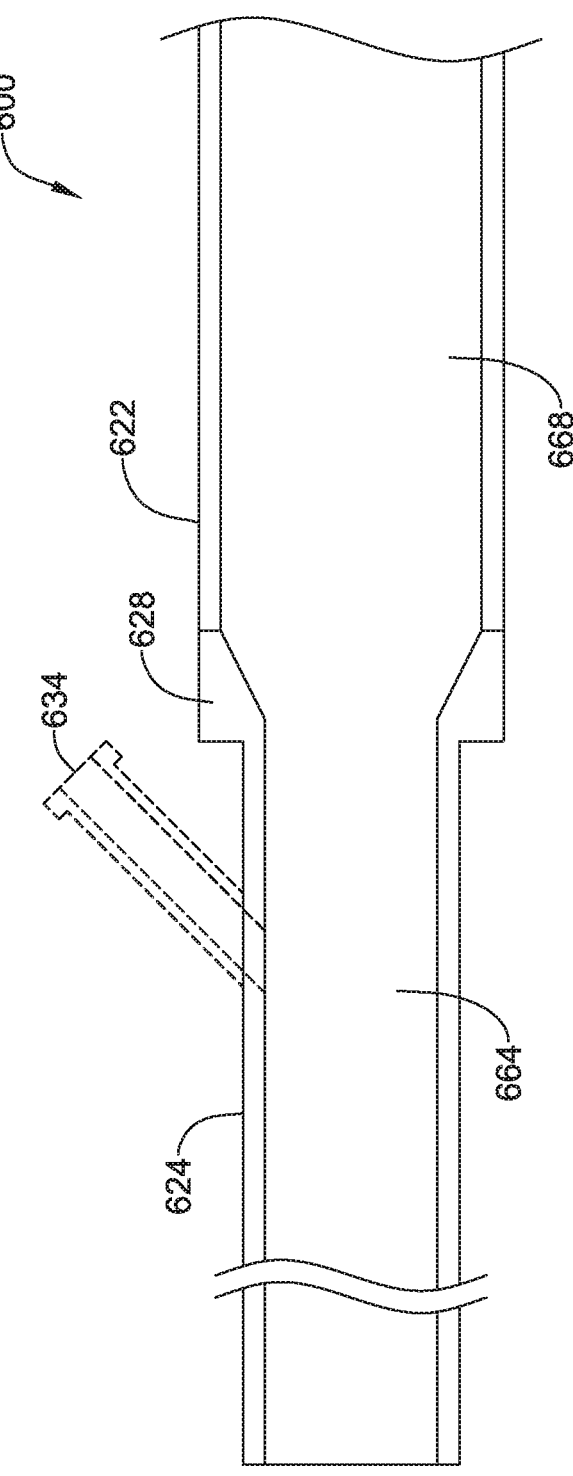

FIGS. 14A and 14B are partially sectioned views of example lumen structure in distal and proximal regions of the guide sheath of FIG. 13.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about", whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to an "embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combined or arranged with each other to form other additional embodiments or to complement and/or enrich the described embodiment(s), as would be understood by one of ordinary skill in the art.

Certain treatments of the body utilizing elongated tubular members such as, but not limited to, introducer sheaths, guide sheaths, catheters, and guide catheters, involve the flow of a dye or contrast fluid through the elongated tubular member to achieve imaging of the treatment site. The following description refers to guide sheaths for simplicity, however it is to be noted that the particular structures are equally applicable to guide catheters and other elongated tubular members. The imaging may be desired before, during, and/or after the treatment procedure is performed. When imaging is desired during a treatment procedure, the imaging fluid may be inserted through a lumen in the guide sheath. As used in this specification and the appended claims, the "diameter" of a lumen is considered to be the inner diameter of the lumen extending through the sheath, catheter, or other elongate tubular member. The flow rate of the fluid through the guide sheath may be affected by the inner diameter of the lumen, any increases or decreases in that diameter, the presence of a treatment device within the lumen, and the location of the treatment device. A first flow rate may be defined as the flow rate of fluid through the guide sheath in the absence of a treatment device, and a second flow rate may be defined as the flow rate of fluid through the guide sheath with a treatment device positioned within the guide sheath. In a traditional guide sheath with a constant diameter lumen, the second flow rate will generally be lower than the first flow rate due to the presence of the treatment device acting as an obstacle to fluid flow. The amount of reduction in the second flow rate as compared to the first flow rate may depend on the size and position of the treatment device. In order to achieve rapid and effective imaging, it may be desired to achieve a second flow rate that approximates (e.g., is the same, substantially the same, considerably the same, essentially the same, to a significant extent the same, etc.) the first flow rate, without removing the treatment device completely from the guide sheath. Achieving a second flow rate that approximates the first flow rate may allow for hand injection of dye due to less pressure being required to force the dye around the treatment device, which may provide an easier, faster procedure without the need for additional machinery. Completely withdrawing the treatment device from the guide sheath while imaging is performed, and then re-inserting the treatment device into the guide sheath may cause damage to the treatment device and may be too time consuming and difficult in relation to the desired parameters of the treatment procedure.

An example of a treatment that may utilize imaging during the procedure is the temporary or permanent interruption or modification of select nerve function. One such treatment is renal nerve ablation, which is sometimes used to treat conditions such as or related to hypertension, congestive heart failure, diabetes, or other conditions impacted by high blood pressure or salt retention. The kidneys produce a sympathetic response, which may increase the undesired retention of water and/or sodium. The result of the sympathetic response, for example, may be an increase in blood pressure. Ablating some of the nerves running to the kidneys (e.g., disposed adjacent to or otherwise along the renal arteries) may reduce or eliminate this sympathetic response, which may provide a corresponding reduction in the associated undesired symptoms (e.g., a reduction in blood pressure). Chronic hypertension that may not be responsive to medication may be improved or eliminated by disabling excessive nerve activity proximate to the renal arteries. Bi-lateral treatment of the two renal arteries may be performed to achieve optimal denervation. Bi-lateral treatment may involve a single treatment device that is used to treat both arteries. The treatment device may be inserted through a guide sheath positioned. Treatment may involve extending the treatment device from the distal end of the guide sheath. After treatment of a first renal artery, the treatment device may be withdrawn from the first renal artery and into the guide sheath, the second renal artery may be imaged by flowing dye or contrast fluid through the guide sheath, and then the treatment device may be extended from the guide sheath and inserted into the second renal artery.

Figure 1:
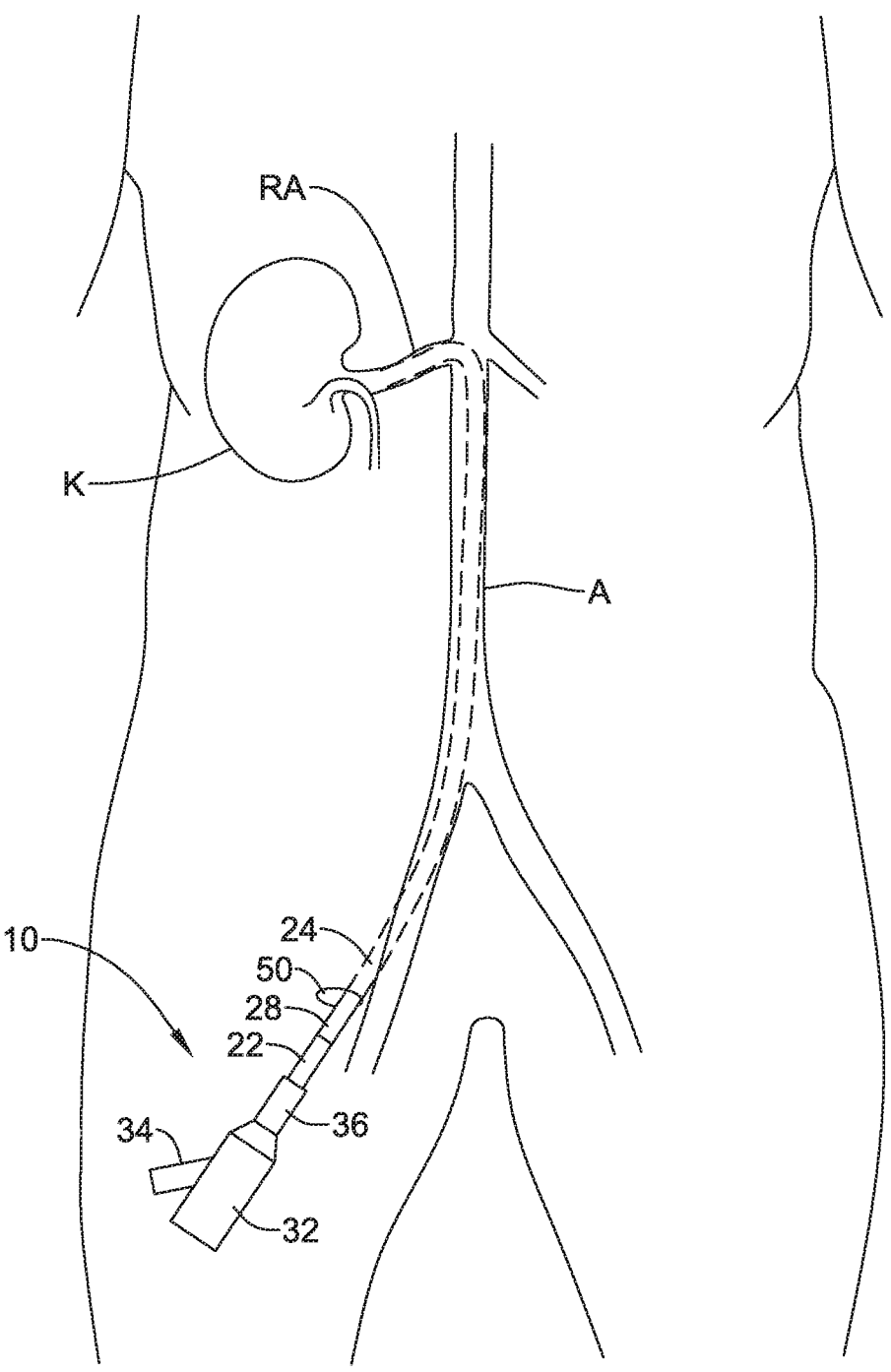
FIG. 1 is a schematic view of an example guide sheath in use.

FIG. 1 is a schematic view of an example guide sheath 10 that may be used to insert a treatment device such as a renal nerve ablation device. The renal nerve ablation device may be used to ablate nerves (e.g., renal nerves) disposed adjacent to the kidney K (e.g., renal nerves disposed about a renal artery RA). In use, the distal region 24 of the guide sheath 10 may be advanced through an incision in the skin 50 and into a blood vessel such as the aorta A to a position within the renal artery RA. A renal nerve ablation device may then be delivered through the guide sheath 10. When positioned as desired, the renal nerve ablation device may be activated to activate one or more electrodes on the ablation device. This may include operatively coupling the renal nerve ablation device to a control unit, which may include an RF generator, so as to supply the desired activation energy to the electrodes. When suitably activated, the electrodes may be capable of ablating tissue (e.g., renal nerves) and sensors may be used to detect desired physical and/or biological parameters.

An exemplary renal nerve ablation device and associated energy delivery methods useable with the embodiments disclosed herein are disclosed in U.S. Patent Application Publication No. 2013/0165926 entitled "METHODS AND APPARATUSES FOR REMODELING TISSUE OF OR ADJACENT TO A BODY PASSAGE", the full disclosure of which is incorporated by reference herein.

Figure 2:
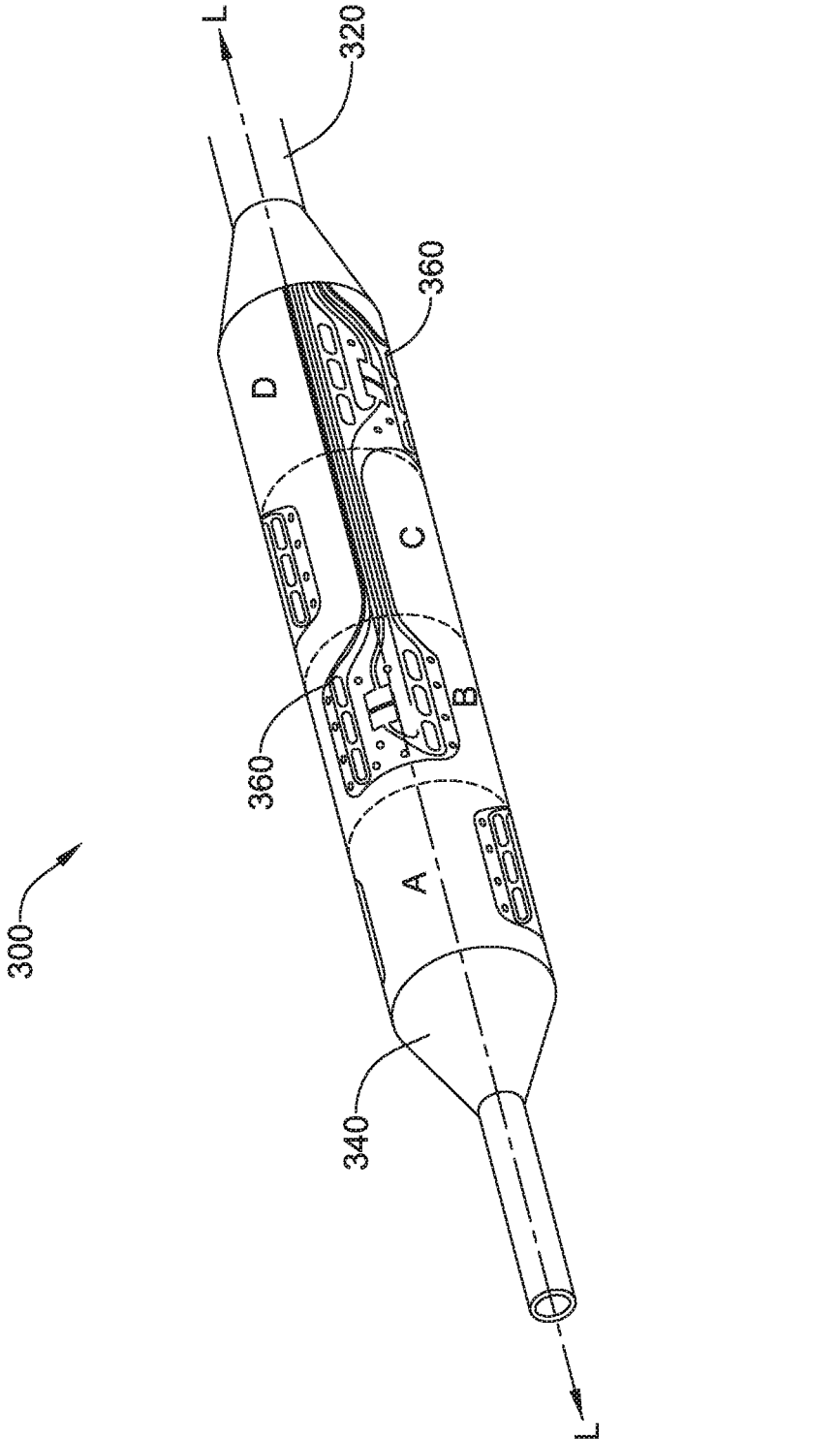
FIG. 2 is a perspective view of an example expandable member of a renal nerve ablation device.

FIG. 2 is a perspective view of an example renal nerve ablation device 300. The renal nerve ablation device 300 may include an elongate tubular member or catheter shaft 320. The catheter shaft 320 may be configured to be slidingly advanced within the guide sheath 10 to a target site. An expandable member 340 may be disposed at, on, about, or near a distal region of the catheter shaft 320. In some embodiments, the expandable member 340 may be self-expanding from a collapsed delivery state to an expanded state, such as a basket, a swellable foam or other material, or a plurality of struts, for example. In some embodiments, the expandable member 340 may be selectively expanded from a collapsed delivery state to an expanded state, such as a compliant, non-compliant, or semi-compliant balloon, for example. In some embodiments, one or more electrodes 360 may be disposed on, disposed about, or coupled to an outer surface of the expandable member 340. In some embodiments, the one or more electrodes may be operatively and/or electrically connected to a control unit and/or an RF generator (not illustrated). In some embodiments, the one or more electrodes may include a plurality of electrode assemblies. In some embodiments, one or more of the plurality of electrode assemblies may be configured to be monopolar or bipolar, and may further include a temperature sensor, for example, a thermistor or thermocouple.

While the devices and methods described herein are discussed relative to renal nerve ablation and/or modulation, it is contemplated that the devices and methods may be used in other treatment locations and/or applications involving insertion of a treatment device through a guide sheath into a body lumen or region, and flow of dye or contrast fluid through the guide sheath without complete removal of the treatment device from the guide sheath. Some example treatment locations may include, but are not limited to: blood vessels, urinary vessels, or in other tissues via trocar and cannula access.

The renal nerve ablation device 300 may be delivered to the treatment site through a guide sheath 10 having a lumen 64. The ablation device 300 may be advanced out of the distal end of the guide sheath 10 and the expandable member 340 may be expanded for treatment. Following treatment with the ablation device 300, the expandable member 340 may be contracted. For example, the expandable member 340 may be deflated via a vacuum source, re-folded or twisted by applying torque to at least a portion of the expandable member 340, or by being withdrawn back into the guide sheath 10.

In use, the ablation device 300 may be advanced through a guide sheath 10 within a blood vessel to a position adjacent to a first target tissue (e.g., within a renal artery). In some embodiments, the target tissue may be one or more renal nerves disposed about the renal artery. When suitably positioned distal of the distal end of the guide sheath 10, expandable member 340 may be expanded from a collapsed delivery configuration to an expanded configuration. This may place the electrodes 360 against the wall of the blood vessel. Ablation energy may be transmitted from the electrode 360 through the target tissue (where renal nerves may be ablated, modulated, or otherwise impacted), in a bipolar or a monopolar configuration.

After treating the first target tissue, such as a first renal artery, the ablation device 300 may be withdrawn from the treatment site, back into the guide sheath 10. In preparation for treating the second target tissue, such as a second renal artery, imaging of the second treatment site using dye or contrast fluid may be desired. The guide sheath may be withdrawn from the first renal artery and inserted into the second renal artery. Dye or contrast fluid may be passed through the guide sheath 10 to provide imaging of the second treatment site, without completely removing the ablation device 300 from the guide sheath 10.

A dye flow rate of 4-5 ml/sec may be considered desirable. A 7 Fr (French) guide sheath may have an inner diameter of around 0.100 inches (0.254 cm) and may have an average dye flow rate of 5.53 ml/sec with the ablation device 300 including the expandable member 340 in the sheath. A minimum desirable flow rate may be >1.5 ml/sec. However, it may be desired to use a 6 Fr guide sheath, which has an inner diameter of around 0.070 inches (0.1778 cm). Without changing the size of the expandable member 340, a reduction in dye flow rate results. For example, a flow rate of 0.80 ml/sec may be achieved with the expandable member in a 55 cm (21.65 inches) 6 Fr guide catheter. When the expandable member is distal to the guide catheter, dye flow rates may range from 0.58 ml/sec for an over the wire device, 1.26 ml/sec for a monorail device in a 140 cm (55.12 inches) guide sheath, and 2.73 ml/sec for a monorail device in a 55 cm (21.65 inches) guide sheath. While the dye flow rates with the expandable member distal of the guide sheath may be improved over the rate with the expandable member inside the guide sheath, the rates are below the desired 4-5 ml/sec rate.

A single ablation device 300 may be used to treat both renal arteries, and withdrawing the ablation device 300 completely from the guide sheath 10 in order to achieve enhanced dye flow is not desirable due to difficulties which may arise in re-inserting the ablation device 300 into the guide sheath.

Figure 3:
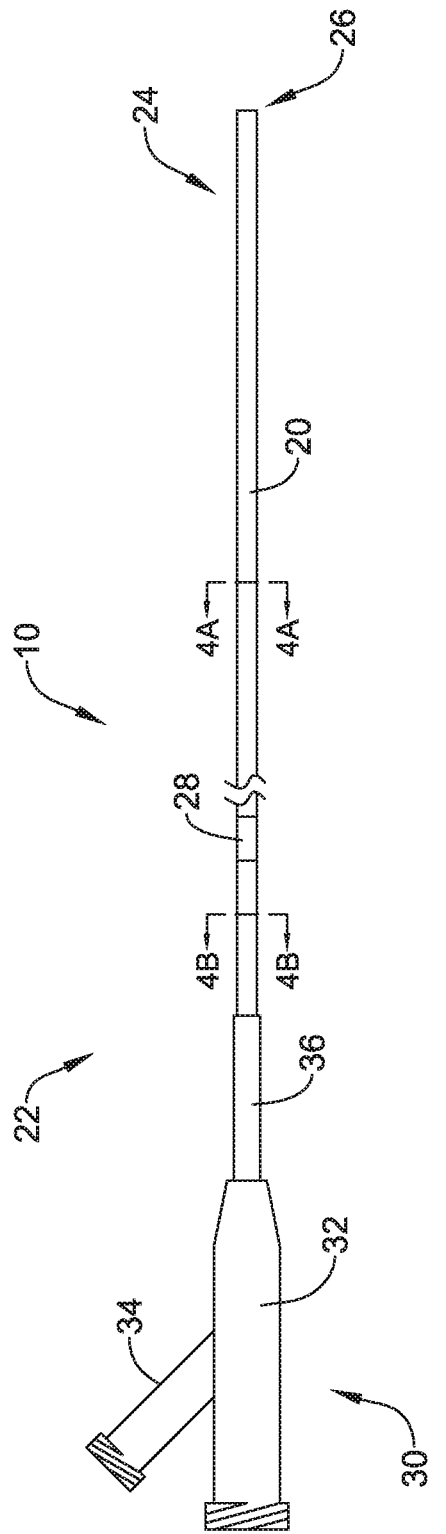
FIG. 3 is a plan view of an example guide sheath.

FIG. 3 is a plan view of a guide sheath 10 in accordance with an embodiment of the invention. In some embodiments, the guide sheath 10 may be used with any of a variety of different catheters, but is preferably used with an intravascular catheter. Examples of intravascular catheters include balloon catheters (including renal denervation catheters), atherectomy catheters, drug delivery catheters, diagnostic catheters and guide catheters. Except as described herein, the guide sheath 10 may be manufactured using conventional techniques and materials.

The guide sheath 10 may be sized in accordance with its intended use. The guide sheath 10 may have a length that is in the range of about 25 cm (about 9.843 inches) to about 150 cm (about 59.06 inches) and may have a diameter that is in the range of about 4 Fr (about 1.333 mm) to about 9 Fr (about 3.0 mm). In some embodiments, the guide sheath 10 may have a length of 25 cm (9.843 inches), 45 cm (17.72 inches), 65 cm (25.59 inches), 90 cm (35.43 inches), 100 cm (39.37 inches), 130 cm (51.18 inches), or 150 cm (59.06 inches), or any length between.

In the embodiment shown in FIG. 3, the guide sheath 10 includes an elongate shaft 20 that has a proximal region 22, a distal region 24, and transition region 28, and a distal end 26. For the purpose of describing the device, the proximal region 22 is considered to be the region of the elongate shaft 20 that remains outside the body during a procedure, and the distal region 24 is considered to be the region of the elongate shaft 20 that is inserted into the body during the procedure. A hub and strain relief assembly 30 may be connected to the proximal region 22 of the elongate shaft 20. The hub and strain relief assembly 30 may include a main body portion 32, a port 34, and a strain relief 36 that is intended to reduce kinking. The hub and strain relief assembly 30 may be of conventional design and may be attached using conventional techniques.

Figure 4A:
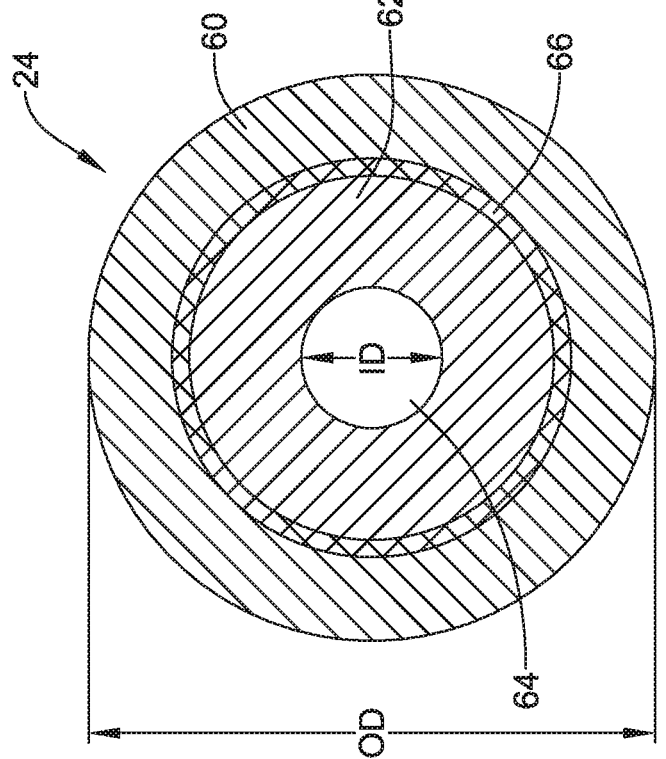
FIGS. 4A and 4B are cross-sectional views of the guide sheath of FIG. 3 taken along lines 4A-4A and 4B-4B, respectively.
Figure 4B:
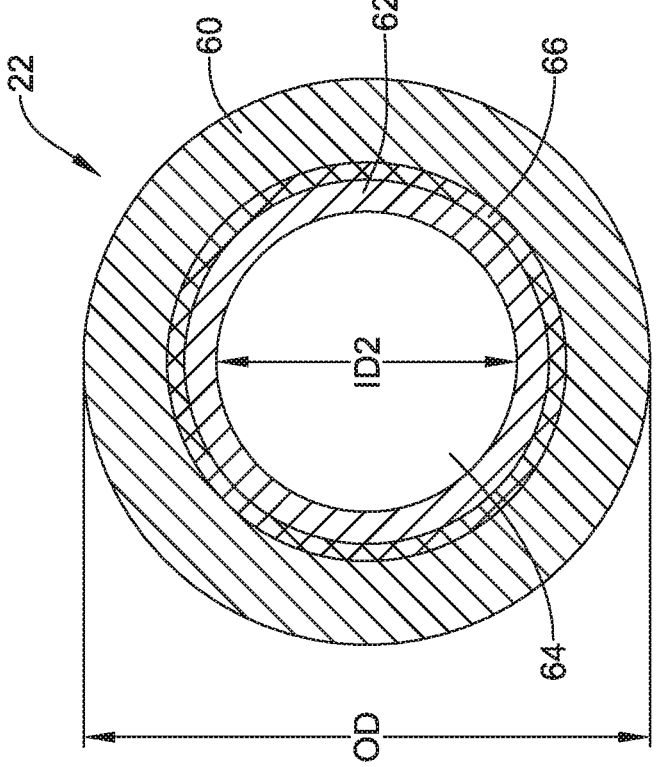

FIG. 4A is a cross-sectional view of one example of the distal region 24 of the elongate shaft 20 taken along line 4A-4A of FIG. 3. The elongate shaft 20 may include an outer layer 60 and an inner layer 62. Each of the outer layer 60 and the inner layer 62 may extend from the proximal region 22 of the elongate shaft 20 to the distal region 24 of the elongate shaft 20. The inner layer 62 defines a lumen 64 that extends through the elongate shaft 20. In some embodiments, the guide sheath 10 has a single lumen 64 and is devoid of other lumens. The lumen 64 has a first inner diameter ID1 in the distal region 24. FIG. 4B is a cross-sectional view of one example of the proximal region 22 of the elongate shaft 20 taken along line 4B-4B of FIG. 3. The lumen 64 has a second inner diameter ID2 in the proximal region 22. The second inner diameter ID2 is greater than the first inner diameter ID1. In some embodiments, the elongate shaft 20 has an outer diameter OD that remains constant over the length of the elongate shaft 20, from the proximal region 22 to the distal region 24. In other embodiments, the outer diameter OD may change over the length of the elongate shaft 20. For example, the outer diameter of the elongate shaft 20 may be greater in the proximal region 22 compared to the distal region 24.

In some embodiments, as shown in FIGS. 4A and 4B, the elongate shaft 20 may include a reinforcement layer 66, such as a braid or ribbon layer to increase particular properties such as kink resistance. The reinforcement layer 66 may be positioned between the outer layer 60 and the inner layer 62 and may provide adequate kink resistance without substantially increasing the overall profile of the elongate shaft 20. Alternatively, a single layer shaft may be utilized. An inflation lumen may also be provided (not illustrated), whether coaxial or in a multi-lumen co-extrusion, for use with a balloon catheter.

Figure 5:
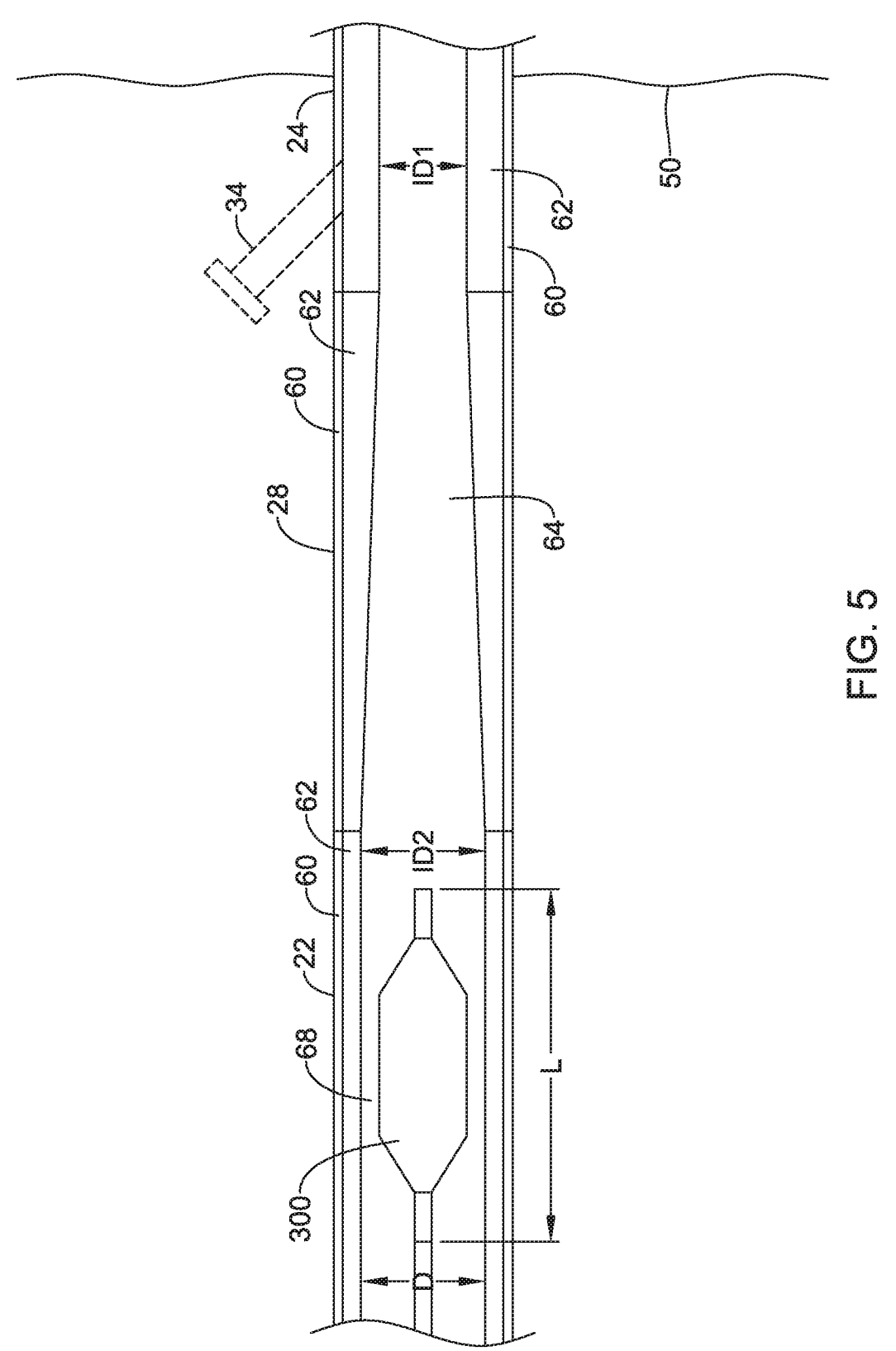
FIGS. 5-7 are partially sectioned views of example guide sheaths showing distal, proximal, and intermediate regions thereof.
Figure 6:
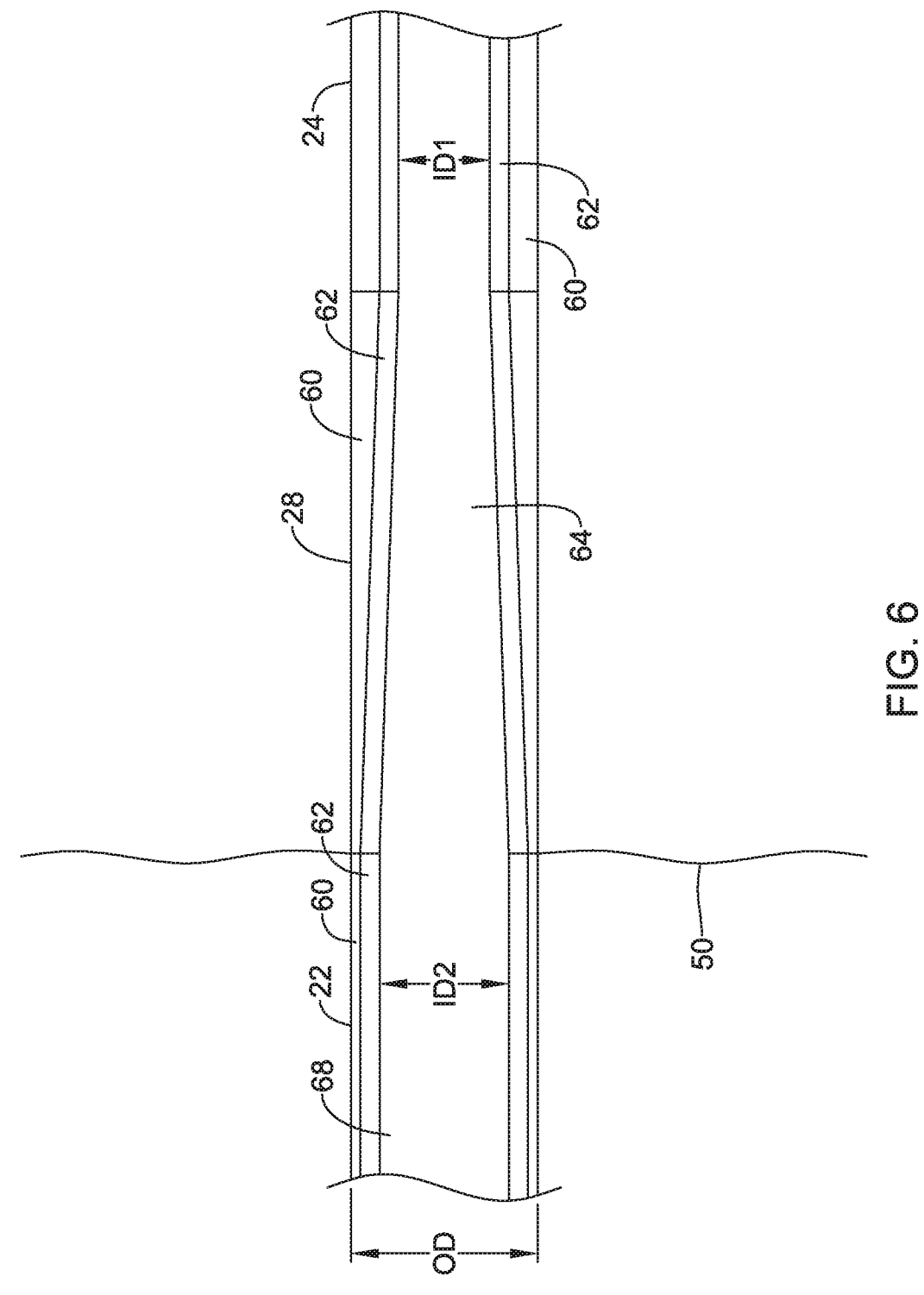
Figure 7:
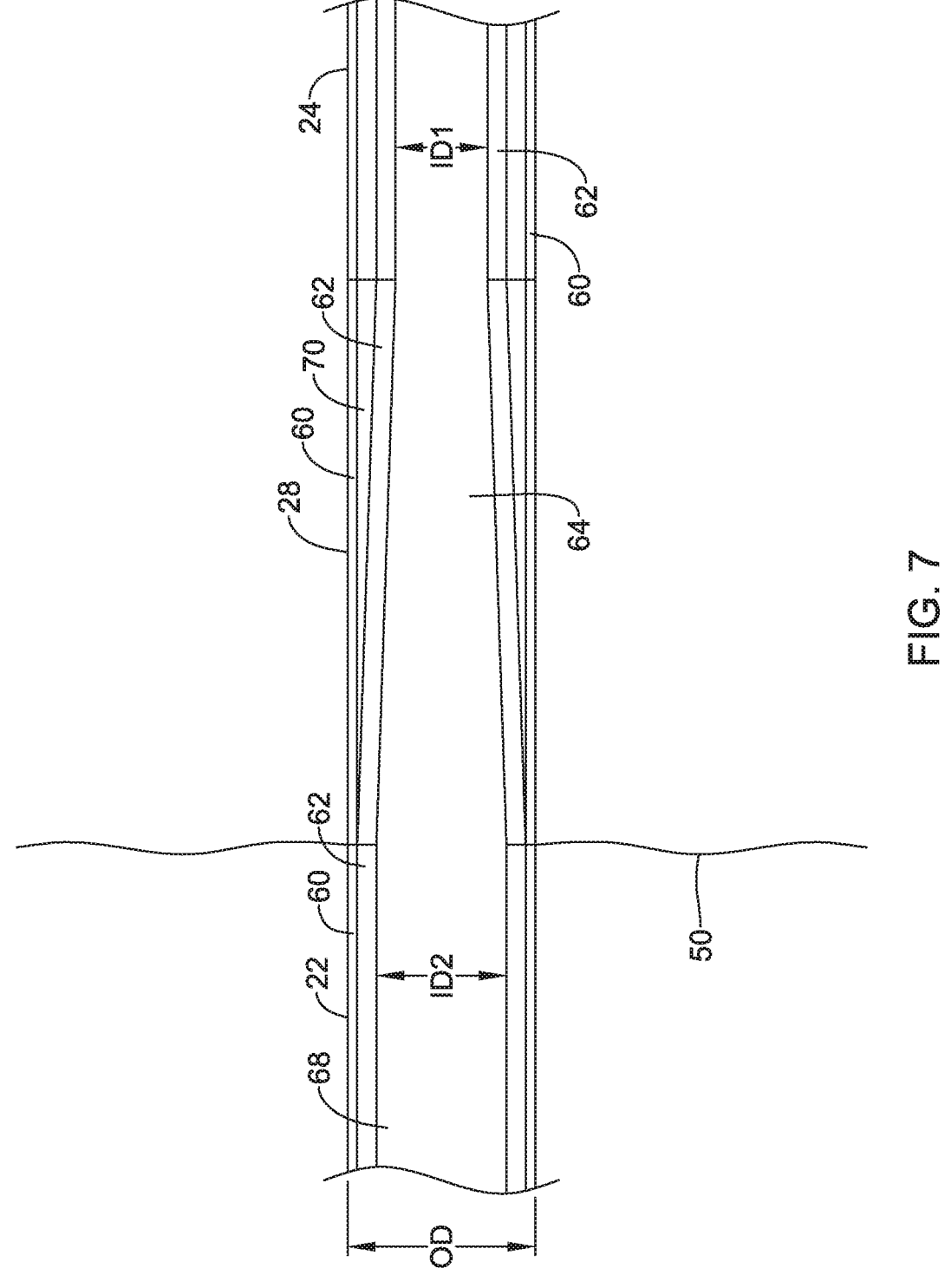

In some embodiments, the lumen 64 in the distal region 24 has a substantially constant first inner diameter ID1 and the lumen 64 in the proximal region 22 has a substantially constant second inner diameter ID2. The elongate shaft 20 may include a transition region 28 located between the proximal region 22 and the distal region 24 in which the lumen 64 transitions from the first inner diameter ID1 to the second inner diameter ID2. In use, the transition region 28 may be positioned outside the body (see FIG. 5) or immediately inside the body (see FIG. 6). FIGS. 5-7 are cross-sectional views of examples of elongate shaft 20, showing the distal end of the proximal region, the transition region 28, and the proximal end of the distal region 24. In the embodiment shown in FIG. 5, the transition region 28 and a portion of the proximal region 22 is positioned proximal of or outside the skin 50. As shown in FIG. 5, the outer layer 60 has a constant thickness along the elongate shaft 20 and the inner layer 62 is thicker in the distal region 24 than in the proximal region 22, with a gradual increase in thickness in the transition region 28.

In the embodiment shown in FIG. 6, the transition region 28 is positioned distal of the skin 50, just inside the body. As shown, the inner layer 62 may have a constant thickness and the thickness of the outer layer 60 may increase in the transition region 28 such that the thickness of the outer layer 60 is greater in the distal region 24 than in the proximal region 22. The outer layer 60 may have an inner diameter that is about equal to the outer diameter of the inner layer 62. In other embodiments (not illustrated), the thicknesses of the inner layer 62 and the outer layer 60 may remain constant over the length of the elongate shaft 20, and an additional layer may be present and may have a changing thickness that achieves the change from inner diameter ID1 to inner diameter ID2. In the embodiment shown in FIG. 7, an intermediate layer 70 may be present in the transition region 28 and the distal region 24, but not in the proximal region 22. The intermediate layer 70 may increase in thickness in the transition region 28, thereby creating the decrease in inner diameter from the second inner diameter ID2 in the proximal region 22 to the first inner diameter ID1 in the distal region 24. In some examples, the intermediate layer 70 may extend from the proximal end to the distal end of the elongate shaft 20. The intermediate layer 70 may have a uniform thickness, and another layer, such as the inner layer 62 or the outer layer 60 may be configured to define the changing inner diameter from ID1 to ID2. Alternatively, another layer may be provided that defines the changing inner diameter from ID1 to ID2. In some examples, the reinforcing layer 66 may increase in thickness in the transition region 28, thereby creating the decrease in inner diameter from ID2 to ID1.

In some embodiments, the lumen 64 in the proximal region 22 defines a parking space 68 configured to contain the treatment device 300, such as a renal nerve ablation device 300. The parking space 68 allows the device 300 to remain within the guide sheath 10 yet have a lesser effect on the flow rate. The parking space 68 may have a diameter D and a length L such that when the treatment device 300 is in the parking space 68, fluid injected through the lumen proximal of the parking space 68 flows around the treatment device 300 and achieves a second flow rate in the distal region 24 that is substantially the same as the first flow rate in the distal region 24. The larger inner diameter ID2 in the proximal region 22 may define the parking space 68. The larger inner diameter ID2 may provide a large enough space for dye or contrast fluid to flow around the device 300, to achieve a flow rate that is substantially the same as the flow rate of the guide sheath 10 without a device 300 inside.

A port 34 may be disposed at the proximal end of the elongate shaft 20, as shown in FIG. 1. The port 34 may be used to inject dye or contrast fluid into the lumen 64 in the proximal region 22, where the lumen has the second, larger inner diameter ID2. Optionally, in any of the embodiments shown in FIGS. 1-7, the port 34 may be a side port disposed distal of the transition region 28, as shown in FIG. 5, allowing dye or contrast fluid to be inserted directly into the lumen 64 distal of the transition region 28, where the lumen has the first, smaller diameter ID1, thus bypassing a treatment device disposed in the parking space 68. The use of a side port 34 disposed distal of the parking space 68 may provide a guide sheath 10 having a first flow rate, without a treatment device, that is substantially the same as a second flow rate with a treatment device disposed in the parking space 68. Dual ports may also be used, with a proximal port 34 disposed near or at the proximal end and a side port 34 disposed distal of the parking space 68. Such a device may provide the user with the options of using either or both of the ports for delivering dye or contrast fluid.

The guide sheath 10 may be used in a method of treatment that involves imaging the treatment site while a treatment device remains within the guide sheath 10. The guide sheath 10 may be inserted through an incision in a patient's skin to the treatment site, and positioned with the distal region 24 within the patient's body and the proximal region 22 outside the body. A treatment device may be inserted through the lumen 64 of the guide sheath and extended distal of the guide sheath to the treatment site. The treatment device may include an element, such as a balloon, that occupies a majority of an area of the lumen. An example treatment device may be a balloon catheter or a renal nerve ablation device 300, where the element is a balloon. After a procedure is performed at the treatment site, the treatment device may be withdrawn to a parking space 68 in the proximal region 22 of the guide sheath 10, outside the body. Imaging fluid may then be injected through the guide sheath lumen 64 while the treatment device remains in the parking space 68 in the proximal region 22 of the guide sheath 10.

Figure 8:
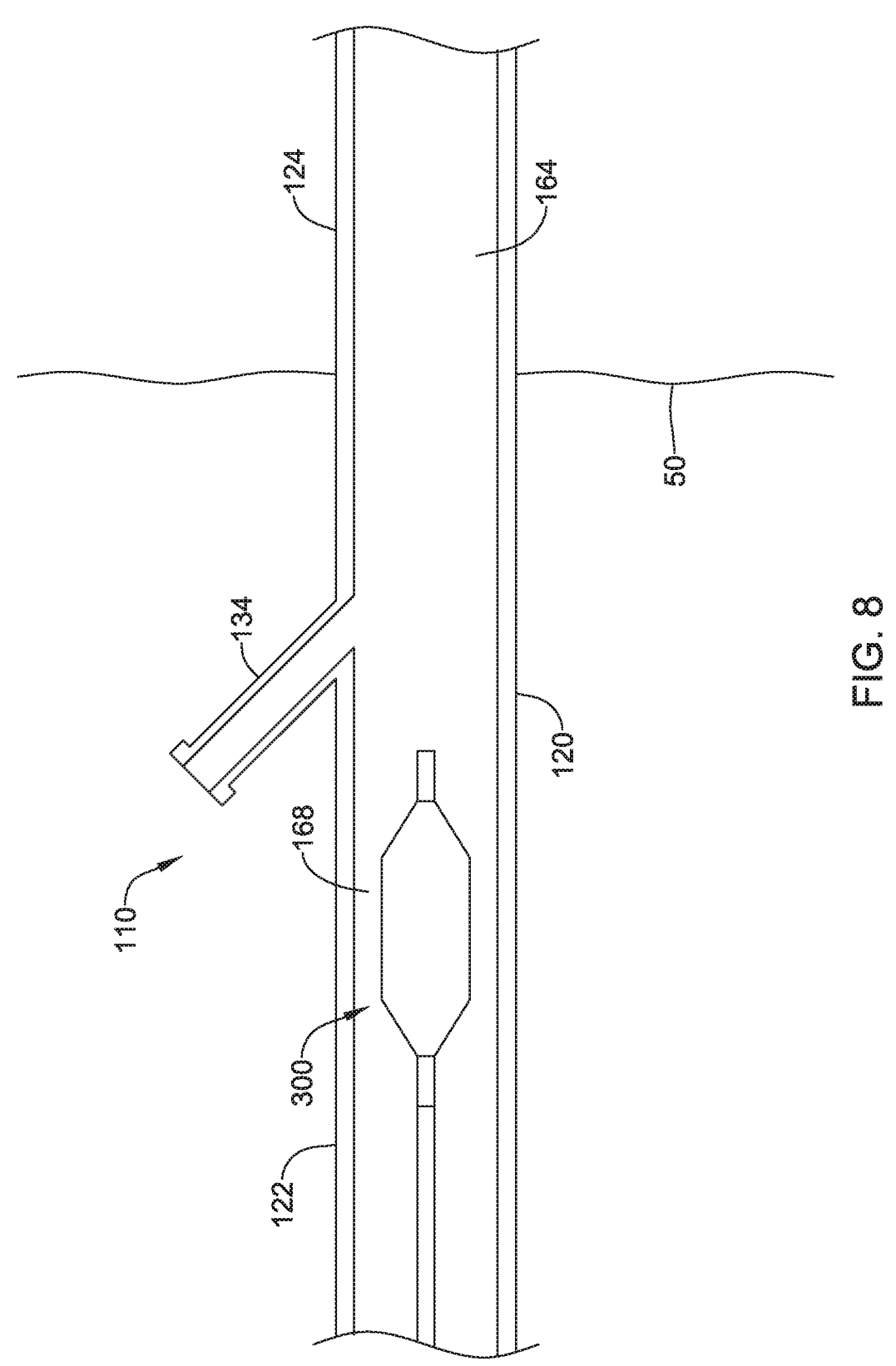
FIGS. 8-9 are partially sectioned views of the distal regions of additional example guide sheaths.

FIG. 8 shows another embodiment of guide sheath 110 that provides enhanced fluid flow of dye or contrast fluid. Guide sheath 110 includes an elongated shaft 120 having a distal region 124 and a proximal region 122. The elongated shaft 120 has a substantially constant diameter lumen 164 throughout its length. A side port 134 disposed at the distal end of the proximal region 122 allows for the introduction of dye or contrast fluid into the lumen 164. In use, a treatment device such as a renal denervation device 300 is withdrawn to a parking space 168, which is a location within the proximal region 122 of the lumen 164, proximal of the side port 134. Dye or contrast fluid may be introduced through the side port 134, without interference from the device 300, providing a flow rate through the distal region 124 substantially the same as if no device 300 were present. A proximal port (not illustrated) may also be provided at the proximal end of the guide sheath 110.

Figure 9:
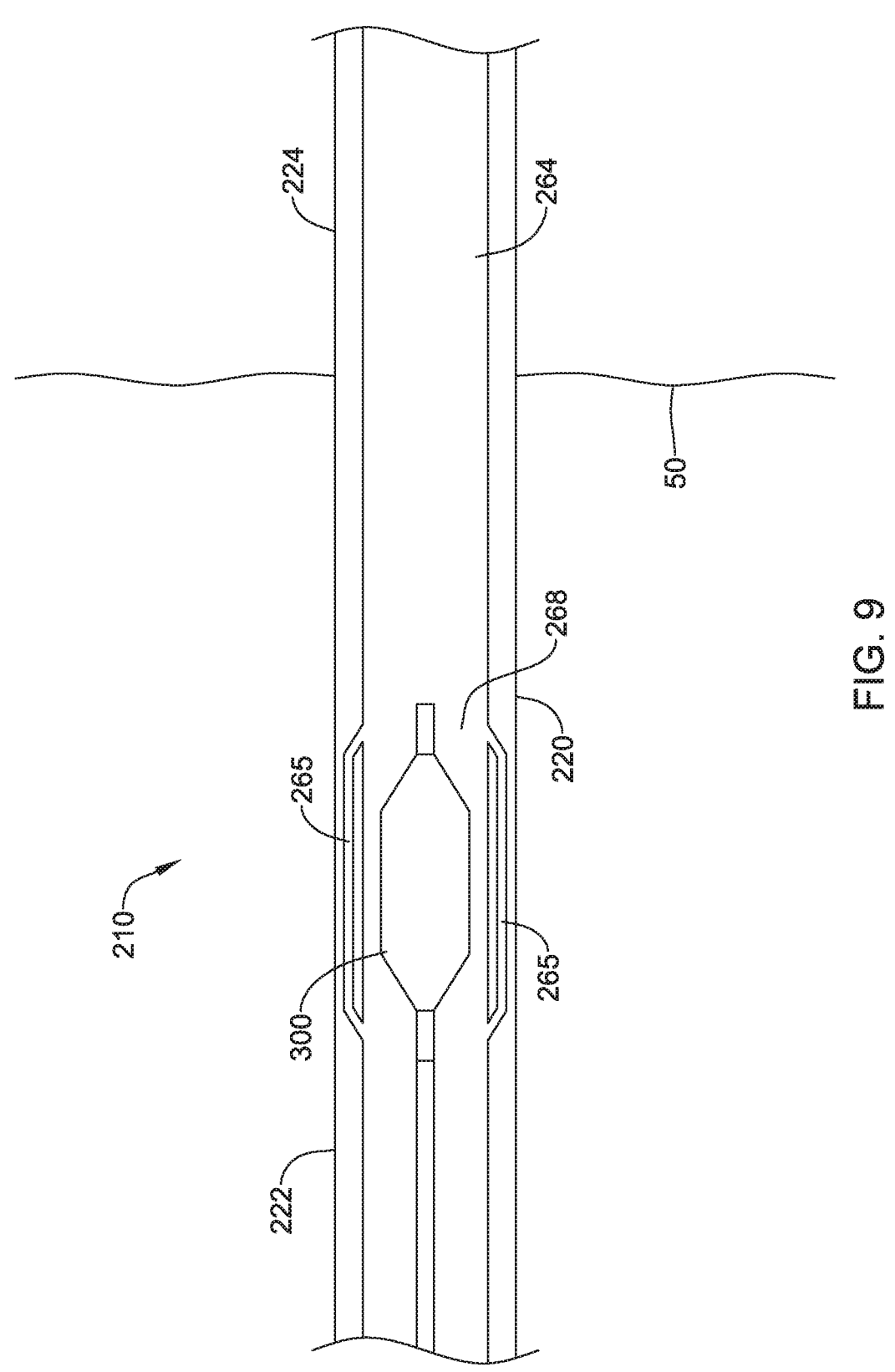

In some embodiments, a guide sheath 210 may have one or more side fluid paths 265 providing a bypass for dye or contrast fluid to flow around a device 300 disposed within a parking space 268 in the proximal region 222 of the elongate shaft 220, proximal of the skin 50. As shown in FIG. 9, the elongate shaft 220 has a lumen 264 extending throughout the proximal region 222 and the distal region 224. The inner diameter of the lumen 264 may be substantially constant throughout the length of the elongate shaft 220. One or more side fluid path 265 may connect regions of the lumen 264 proximal and distal of a parking space 268 to provide a bypass for fluid around a device 300 disposed within the parking space 268. As shown in FIG. 9, two side fluid paths 265 may be disposed spaced apart from each other in the elongate shaft 220. The side fluid paths 265 may extend adjacent to the lumen 264. As shown in FIG. 9, the side fluid paths 265 may be substantially parallel to the lumen 264. Each side fluid path 265 may join a first location of the lumen 264 to a second location of the lumen 264, where the first and second locations are spaced apart axially along the guide sheath 210. One or more side fluid path 265 may extend from proximal of the parking space 268 to distal of the parking space 268 along a helical path. Alternatively, two or more side fluid paths 265 may extend in a crisscross or random pattern across the parking space 268. A length of the side fluid paths 265 may be at least as long as an expandable member to be used with the guide sheath 210. In some embodiments the first and second locations may be spaced apart about 4 cm (about 1.575 inches) to about 6 cm (about 2.362 inches) along the lumen. In some embodiments, the first location is proximal of the second location and the first location is spaced about 3 cm (about 1.181 inches) to about 15 cm (about 5.906 inches) from a proximal end of the guide sheath and/or is spaced about 30 cm (about 11.81 inches) to about 50 cm (about 19.69 inches) from a distal end of the guide sheath. In other embodiments, the first location is about 5 cm (about 1.969 inches) to 10 cm (3.937 inches) from the proximal end of the guide sheath. When dye or contrast fluid is injected through a port at the proximal end of the guide sheath 210, some fluid may flow around the device 300 disposed in the parking space 268, and some fluid may flow through the side fluid paths 265, bypassing the device 300. The side fluid paths 265 may provide enhanced fluid flow that approaches a fluid flow without a device 300 present in the guide sheath 210. A side port (not illustrated) may be provided distal of the parking space 268 as an alternative to or in addition to a proximal port.

Figure 10:
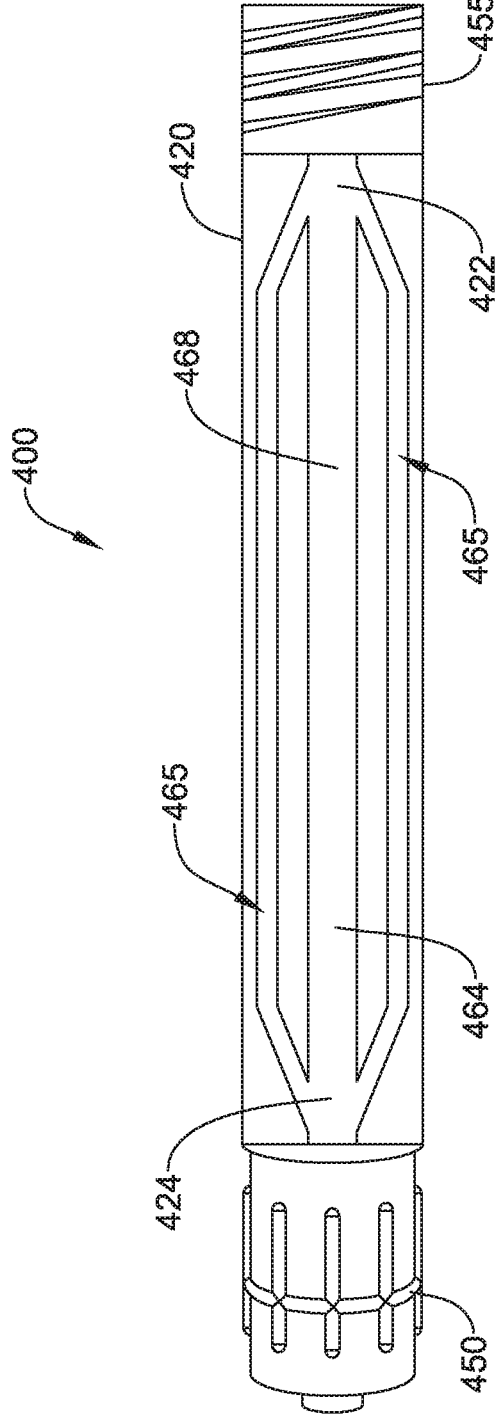
FIG. 10 is a partial cut-away view of an example accessory device.

FIG. 10 shows an accessory device 400 connectable to a proximal end of a guide sheath (not illustrated). The accessory device 400 may include an elongate body 420 with a distal region 424, a proximal region 422, and a lumen 464 extending through the length of the elongate body 420. The lumen 464 may provide a parking space 468 for a device (not illustrated) to be withdrawn from the guide sheath without removing the device completely. The accessory deice 400 may include one or more side fluid path 465 extending substantially parallel to the lumen 464. Each side fluid path 465 may join a first location of the lumen 464 to a second location of the lumen 464, wherein the first and second locations are spaced apart axially along the lumen 464. The side fluid paths 465 connect the distal region 424 of the lumen 464 to the distal region 424 of the lumen 464. The side fluid paths 465 may provide a fluid bypass around the parking space 468.

The accessory device 400 may include a distal connector 450 for attaching the accessory device 400 to the hub of a guide sheath, and a proximal connector 455 for attaching a fluid source to the accessory device 400. The proximal connector 455 may include a proximal port (not illustrated). Alternatively the distal connector 450 may include a distal port (not illustrated), or the accessory device 400 may include both a distal and a proximal port (not illustrated). The lumen 464 may have a diameter that is substantially the same as or greater than the diameter of the lumen of a guide sheath and hub to which the accessory device 400 will be attached. The accessory device 400 may be used with a balloon catheter or other medical device having an enlarged diameter relative to the catheter on which the medical device is disposed.

In use, the balloon or medical device catheter is inserted through a guide sheath. The accessory device 400 may be attached to a proximal hub of the guide sheath prior to or after insertion of the medical device catheter, depending on the features present on the proximal end of the medical device catheter. After a first treatment procedure, if the procedure requires use of dye or contrast fluid prior to complete withdrawal of the medical device catheter, the medical device catheter is withdrawn until the balloon is disposed in the parking space 468. Dye or contrast fluid may be inserted through the proximal region 422 of the lumen 464. The parking space 468 allows the dye or contrast fluid to flow partially through the lumen 464, around the balloon, and to flow partially through the one or more side fluid paths 465, thereby bypassing the balloon disposed within the parking space 468. The bypass side fluid paths 465 provide for a greater fluid flow around the balloon in the parking space 468 as compared to fluid flowing only around the balloon in a single lumen. The length of the side fluid paths 465 may be at least as long as the balloon to be inserted through the guide sheath.

In some embodiments, the combined cross-sectional area of the one or more side fluid paths 465 is equal to or greater than the cross-sectional area of the lumen 464 to provide the same or greater flow rate through the accessory device as compared to the flow rate in the absence of the medical device catheter. After imaging, the medical device may once again be moved distally through the guide catheter for additional treatment.

Figure 11:
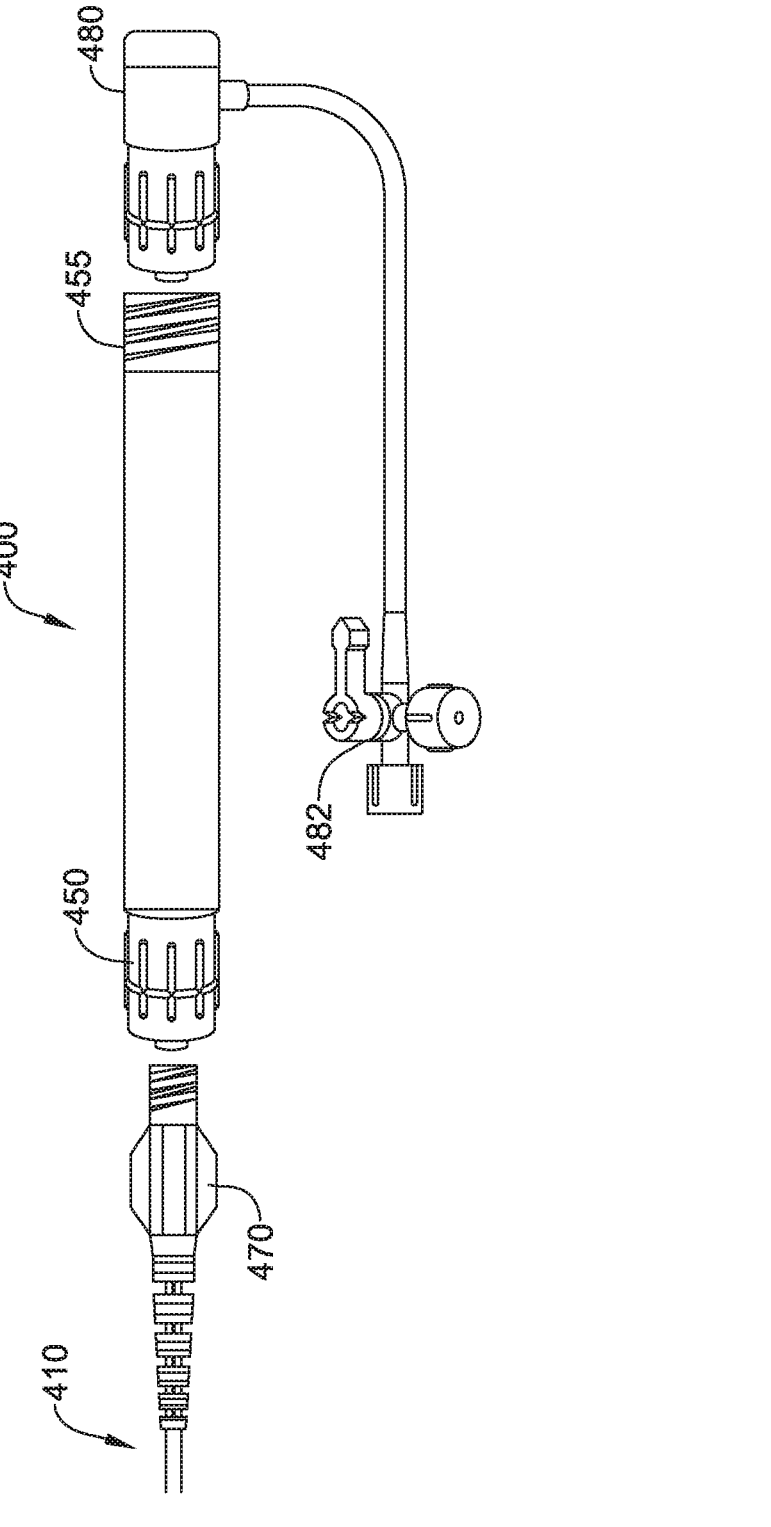
FIGS. 11-12 are perspective views of example accessory devices.

A fluid connector 480 may be attached to the proximal connector 455 of the accessory device 400, and the distal connector 450 of the accessory device 400 may be connected to a proximal luer lock type connector 470 on a guide sheath 410, as shown in FIG. 11. The fluid connector 480 may include one or more fluid valves 482 providing a proximal port, and may be connected to one or more sources of fluid.

Figure 12:
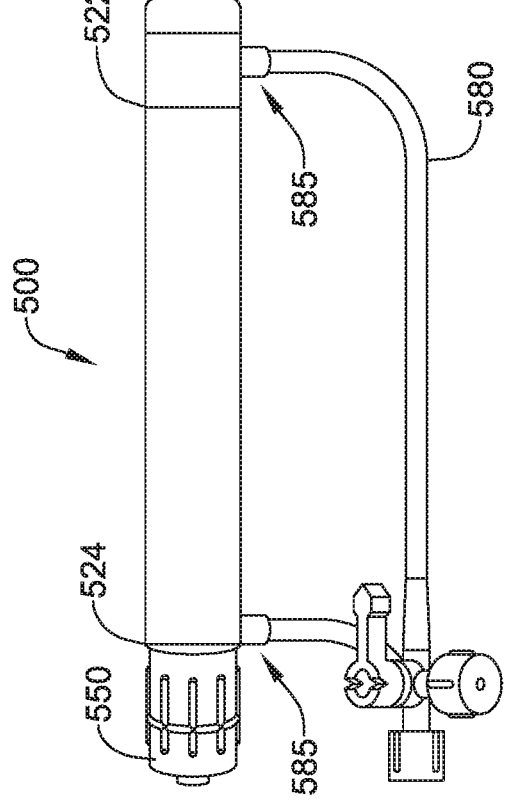

FIG. 12 shows another accessory device 500 with two integrated flush ports 585, one disposed near the distal region 524 and one near the proximal region 522. The accessory device 500 may contain the same interior structure as the accessory device 400, including an inner lumen, parking space, and side fluid paths. In other embodiments, the accessory device 500 may have a single inner lumen (not illustrated) with a diameter that is greater than an inner lumen diameter of the guide sheath to which it is attached. Such an embodiment may include a transition region at the distal end in which the inner diameter of the guide sheath increases to the larger inner diameter within the body of the accessory device 500. The transition region may be similar to that shown in the embodiments of FIGS. 5-7. Accessory device 500 may have a luer lock type connector 550 at its distal end, for attaching to a proximal end of a guide sheath (not illustrated). The dual flush ports 585 of accessory device 500 may provide selective flushing of just the accessory device lumen and side fluid paths, without introducing fluid into the guide catheter.

Another embodiment of guide sheath 600 is shown in FIG. 13. Guide sheath 600 may include a distal region 624, configured to be disposed within the body during use, a proximal region 622, configured to be disposed outside the body, a strain relief 636, and a hub 632. The guide sheath 600 may have at least one lumen 664 having an inner diameter. FIGS. 14A and 14B are partial cross sectional views of guide sheath 600 with alternative transitions between a smaller diameter of the lumen 664 in the distal region 624 and a larger diameter of the lumen 664 in the proximal region 622. The larger lumen diameter in the proximal region 622 may provide a parking space 668 configured to receive the balloon portion of a balloon catheter. As shown in FIG. 14B, the guide sheath 600 may include a transition region 628, providing a transition between the smaller inner diameter of the lumen 664 in the distal region 624 to the larger inner diameter of the lumen 664 in the proximal region 622. The structure of the transition region 628, including inner, outer, and intermediate layers may be similar to that shown in the embodiments of FIGS. 5-7.

In other embodiments, such as shown in FIG. 14A, no transition region is present, and the inner diameter of the lumen 664 steps directly from a smaller diameter in the distal region 624 to a larger diameter in the proximal region 622. The outer diameter of the guide sheath 600 in the distal region 624 may be smaller than the outer diameter of the guide sheath 600 in the proximal region 622. The outer diameter in the distal region 624 may be consistent along its length, and the outer diameter in the proximal region 622 may be consistent along its length, as shown in FIG. 13. The wall thickness of the guide sheath 600 may be consistent along its length, with the increase in lumen inner diameter creating the increase in sheath outer diameter. See FIG. 14A. In other embodiments (not illustrated) the outer diameter of the guide sheath 600 may increase gradually along the length of the guide sheath 600, from a smaller diameter at the distal end, to a larger diameter at the proximal end.

FIGS. 14A and 14B also show an optional side port 634 that may be included in the guide sheath 600, near the proximal end of the distal region 624. The side port 634, if present, may provide for the introduction of dye or contrast fluid distal of the parking space 668, where the medical device will be parked during imaging. Introduction of the dye or contrast fluid directly into the smaller diameter lumen 664 in the distal region 624 may allow for more dye to be delivered with less pressure. The side port 634 may allow for hand injection of the dye. Delivering dye directly into the smaller diameter lumen 664 may provide a flow rate similar to the flow rate achieved without the balloon catheter present. If no side port 634 is present, dye or contrast fluid may be introduced to the lumen 664 at the proximal end of the guide sheath 600. The larger inner diameter of the lumen 664 in the proximal region 622 provides a significant increase in fluid flow around the medical device parked in the parking space 668.

In some embodiments (not illustrated), the guide sheath 10, 110, 210 may include an elongate shaft 20 with one or more shaft segments having varying degrees of flexibility. For simplicity, the following description of the elongate shaft 20 of a guide sheath 10 will reference elongate shaft 20 of guide sheath 10. However, it will be understood that the following description may be equally applicable to the embodiments of guide sheath 110, 210. For example, the elongate shaft 20 may include a proximal segment, an intermediate segment and a distal segment. In some embodiments, the elongate shaft 20 may also include a distal tip segment that may be formed from a softer, more flexible polymer. The elongate shaft 20 may include more than three segments, or the elongate shaft 20 may include fewer than three segments.

If the elongate shaft 20 has, for example, three segments such as a proximal segment, an intermediate segment and a distal segment, each segment may include an inner layer 62 that is the same for each segment and an outer layer that becomes increasingly more flexible with proximity to the distal end of the elongate shaft 20. For example, the proximal segment may have an outer layer that is formed from a polymer having a hardness of 72D (Durometer), the intermediate segment may have an outer layer that is formed from a polymer having a hardness of 68D and the distal segment may be formed from a polymer having a hardness of 46D.

If the elongate shaft 20 has three segments, each of the segments may be sized in accordance with the intended function of the resulting guide sheath 10. For example, the proximal segment may have a length of about 35 inches (about 88.9 cms), the intermediate segment may have a length that is in the range of about 2 inches (about 5.08 cms) to about 3 inches (about 7.62 cms), and the distal segment may have a length that is in the range of about 1 inch (about 2.54 cms) to about 1.25 inches (about 3.175 cms). The inner layer 62 may be a uniform material and may define a lumen 64 that may run the entire length of the elongate shaft 20 and that is in fluid communication with a lumen (not illustrated) extending through the strain relief assembly 30. The lumen 64 defined by the inner layer 62 may provide passage to a variety of different medical devices such as a renal denervation ablation device 300 (see FIG. 2), and thus the inner layer 62 may include, be formed from, or be coated with a lubricious, hydrophilic, hydrophobic, and/or protective material. For example, lubricious coatings may reduce friction within the lumen 64 and aid in insertion and steerability of devices within the lumen 64 of the guide sheath 10. An exemplary material is polytetrafluoroethylene (PTFE), better known as TEFLON®. However, one of skill in the art would recognize other materials having desirable characteristics.

The inner layer 62, outer layer 60 and/or intermediate layer 70 may be dimensioned to define a lumen 64 in the distal region 24 having an appropriate inner diameter to accommodate its intended use. In some embodiments, the lumen 64 in the distal region 24 has a diameter of about 0.070 inches (about 0.1778 cm) to about 0.100 inches (about 0.254 cm).

The guide sheath 10 may comprise any suitable material. Some examples of suitable materials include metals, metal alloys, polymers, or the like, or combinations, blends, or mixtures thereof. The outer layer 60 may be formed from any suitable polymer that will provide the desired strength, flexibility or other desired characteristics. Polymers with low durometer or hardness may provide increased flexibility, while polymers with high durometer or hardness may provide increased stiffness. In some embodiments, the polymer material used is a thermoplastic polymer material. Some examples of some suitable materials include polyurethane, elastomeric polyamides, block polyamide/ethers (such as PEBAX®), silicones, and co-polymers. The outer layer 60 may be a single polymer, multiple layers, or a blend of polymers. By employing careful selection of materials and processing techniques, thermoplastic, solvent soluble, and thermosetting variants of these materials may be employed to achieve the desired results.

In particular embodiments, a thermoplastic polymer such as a co-polyester thermoplastic elastomer such as that available commercially under the ARNITEL® name may be used. In some embodiments, part or all of the outer layer 60 may include materials added to increase the radiopacity of the outer layer 60, such as 50% bismuth subcarbonate.

Some examples of suitable polymeric materials may include, but are not limited to, polyurethane, polyamide, high density polyamide (HDPE), low density polyamide (LDPE), polyether block amide (PEBA), polyethylene, polytetrafluoroethylene (PTFE), and their copolymers, combinations, blends, and mixtures thereof. However, other materials not expressly disclosed may be used in forming the guide sheath 10, or portions thereof.

In some embodiments, the inner layer 62 and the outer layer 60 may each include a polymeric material, such as, but not limited to, any of the polymer materials described herein. For example, in some embodiments the inner layer 62 may include a lubricious polymeric material, such as high density polyethylene (HDPE) or polytetrafluoroethylene (PTFE), thus imparting lubricity to the inner surface of the guide sheath 10. In some embodiments, the outer layer 60 may include a polyamide, or a polyether block amide (PEBA). Different portions or segments of the elongate shaft 20 may include dissimilar materials and/or materials having different durometers and/or flexibilities, thus imparting a plurality of regions having dissimilar flexibilities along the length of the elongate shaft 20.

In some embodiments, the reinforcement layer 66 may include one or more filaments, such as ribbon members, helically wound or coiled around the inner layer 62. In other embodiments, the reinforcement layer 66 may include one or more braid members, such as one or more braids having interwoven opposingly helically wound filaments disposed on the inner layer 62. The reinforcement layer 66 may provide the elongate shaft 20 with a desired degree of kink resistance, yet provide sufficient flexibility for navigation through a tortuous anatomy.

As noted, the medical devices in accordance with the present invention may be of conventional materials and construction, except as described herein. The medical devices described herein may be partially or completely coated with a lubricious or other type of coating. Hydrophobic coatings such as fluoropolymers provide a dry lubricity that may improve handling and device exchanges. An example of a suitable fluoropolymer is polytetrafluoroethylene (PTFE), better known as TEFLON®.

Lubricious coatings may improve steerability and improve lesion crossing capability. Examples of suitable lubricious polymers include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. In some embodiments, a distal portion of a composite medical device may be coated with a hydrophilic polymer as discussed above, while the more proximal portions may be coated with a fluoropolymer.

The medical devices described herein may include, be made with, or be doped with, radiopaque material. Radiopaque materials are understood to be materials capable of producing a relatively bright image on a fluoroscopy screen or another imaging technique during a medical procedure. This relatively bright image aids the user of the device in determining its location. Some examples of radiopaque materials may include, but are not limited to, gold, platinum, palladium, tantalum, tungsten alloy, polymer material loaded with a radiopaque filler, barium subcarbonate powder, and the like, and mixtures thereof. In some embodiments, radiopaque material may be dispersed within the polymers used to form the particular medical device. Additionally, other radiopaque marker bands and/or coils may also be incorporated into the design of the guide sheath 10.

The guide sheath 10 and the various components thereof may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath may be blended with a liquid crystal polymer (LCP). For example, the mixture may contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic (i.e., pseudoelastic) nitinol; other nickel alloys such as nickel-chromium-molybdenum alloys (e.g., UNS: N06625 such as INCONEL® 625, TNS: N06022 such as HASTELLOY® C-22®, TNS: N10276 such as HASTELLOY® C276®, other HASTELLOY® alloys, and the like), nickel-chromium-iron alloy; cobalt alloy; tungsten or tungsten alloys; nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si) and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials may be distinguished from other linear elastic materials such as stainless steel (that may also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In some embodiments, a degree of Magnetic Resonance Imaging (MRI) compatibility may be imparted into the guide sheath 10. For example, portions of device, may be made of a material that does not substantially distort the image and create substantial artifacts (i.e., gaps in the image). Certain ferromagnetic materials, for example, may not be suitable because they may create artifacts in an MRI image. In some of these and in other embodiments, portions of the guide sheath 10 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An apparatus comprising a catheter and a device that comprises an expandable element, comprising:

an elongate member having a distal region and a proximal region, the distal region configured to be disposed within a patient's body and the proximal region configured to be disposed outside a patient's body, the elongate member having a lumen extending therethrough, wherein the device is insertable through the lumen; and a port in fluid communication with the lumen, the port disposed at a proximal end of the proximal region, and the port configured to inject fluid into the lumen, wherein the expandable element occupies a majority of a cross-sectional area of the lumen, wherein the lumen in the proximal region defines a space configured to contain the expandable element within the lumen but external to the patient's body, the space having a diameter and a length such that when the expandable element is in the space, fluid injected through the lumen proximal of the space flows around an outside of the expandable element and such that withdrawing the expandable element into the space from the distal region results in an increase in flow of injected fluid around the expandable element.

2. The apparatus of claim 1, wherein the elongate member includes a transition region between the proximal region and the distal region, wherein the lumen has a first diameter in the distal region and a second diameter in the proximal region, wherein the second diameter is larger than the first diameter, wherein the diameter of the lumen in the transition region increases between the first and second diameters.

3. The apparatus of claim 2, wherein the elongate member has an outer layer, and inner layer, and an intermediate layer, wherein the outer and inner layers extend along the distal region, the transition region, and the proximal region, and the intermediate layer extends from the transition region through the distal region, wherein the intermediate layer provides a change in lumen diameter from the first diameter to the second diameter.

4. The apparatus of claim 1, wherein the catheter further comprises a side port positioned distal of the space.

5. The apparatus of claim 1, wherein the lumen has a constant diameter throughout the distal and proximal regions, the catheter further comprising one or more side fluid path in the proximal region, the one or more side fluid path extending adjacent to the lumen and joining a first location of the lumen to a second location of the lumen, wherein the first location is distal of the space and the second location is proximal of the space.

6. The apparatus of claim 5, wherein the one or more side fluid path, the space, and the port are disposed in an accessory device configured to be coupled to a proximal end of the elongate member, the accessory device having an accessory lumen sized and shaped to match the lumen in the elongate member, wherein the one or more side fluid path is disposed adjacent to the accessory lumen.

7. The apparatus of claim 1, wherein the proximal region has a length of 10 cm to 15 cm and the distal region has a length of 40 cm to 50 cm.

8. The apparatus of claim 1, wherein the elongate member is devoid of lumens in addition to the lumen.

9. The apparatus of claim 1, wherein the elongate member has a first outer diameter in the distal region and a second outer diameter in the proximal region, wherein the second outer diameter is larger than the first outer diameter.

10. The apparatus of claim 1, wherein the expandable element is a balloon.

11. An apparatus comprising a catheter and a device that comprises an expandable element, the catheter comprising:

an elongate member having a distal region configured to be disposed within a patient's body and a proximal region configured to be disposed outside a patient's body, and a lumen extending therebetween, wherein the device is insertable through the lumen, wherein the expandable element occupies a majority of a cross-sectional area of the lumen, and wherein the lumen defines a space configured to contain the expandable element;

a port in fluid communication with the lumen, the port disposed at a proximal end of the proximal region, and the port configured to inject fluid into the lumen; and one or more side fluid path in the proximal region, the one or more side fluid path extending adjacent to and outside the lumen and joining a first location of the lumen to a second location of the lumen, wherein the first and second locations are spaced apart axially along the lumen, wherein the first location is distal to the space, and wherein the second location is proximal to the space.

12. The apparatus of claim 11, wherein the first and second locations are spaced apart 4 cm to 6 cm along the lumen.

13. The apparatus of claim 11, wherein the first location is proximal of the second location and the first location is spaced 5 cm to 10 cm from a proximal end of the elongate member.

14. The apparatus of claim 11, wherein the one or more side fluid path includes first and second side fluid paths, wherein a combined cross-sectional area of the first and second side fluid paths is equal to or greater than a cross-sectional area of the lumen in the distal region.

15. The apparatus of claim 11, wherein the expandable element is a balloon.

\* \* \* \* \*